(12) United States Patent
Gausche-Hill et al.

(10) Patent No.: US 10,850,055 B2
(45) Date of Patent: Dec. 1, 2020

(54) ADJUSTABLY CONTROLLING RESCUE OR ASSISTED BREATHS

(71) Applicant: Los Angeles BioMedical Research Institute at Harbor-UCLA Medical Center, Torrance, CA (US)

(72) Inventors: Marianne Gausche-Hill, Hermosa Beach, CA (US); Timothy Horeczko, San Pedro, CA (US)

(73) Assignee: Los Angeles Biomedical Research Institute, Torrance, CA (US)

( * ) Notice: Subject to any disclaimer, the term of this patent is extended or adjusted under 35 U.S.C. 154(b) by 495 days.

(21) Appl. No.: 15/547,297

(22) PCT Filed: Jan. 29, 2016

(86) PCT No.: PCT/US2016/015803
§ 371 (c)(1),
(2) Date: Jul. 28, 2017

(87) PCT Pub. No.: WO2016/123562
PCT Pub. Date: Aug. 4, 2016

(65) Prior Publication Data
US 2018/0021533 A1 Jan. 25, 2018

Related U.S. Application Data

(60) Provisional application No. 62/109,181, filed on Jan. 29, 2015.

(51) Int. Cl.
*A61M 16/00* (2006.01)
*A61M 16/04* (2006.01)
(Continued)

(52) U.S. Cl.
CPC ...... *A61M 16/0084* (2014.02); *A61M 16/009* (2013.01); *A61M 16/04* (2013.01);
(Continued)

(58) Field of Classification Search
CPC ............ A61M 16/0084; A61M 16/201; A61M 16/009; A61M 16/04; A61M 16/06; A61M 16/0816; A61M 16/20; A61M 16/161
See application file for complete search history.

(56) References Cited

U.S. PATENT DOCUMENTS 5,301,667 A * 4/1994 McGrail ............. A61M 16/208
128/205.13
5,628,305 A * 5/1997 Melker ............. A61M 16/0048
128/202.29
(Continued)

*Primary Examiner* — Michael J Tsai
*Assistant Examiner* — Nathan M Le
(74) *Attorney, Agent, or Firm* — K&L Gates LLP; Louis C. Cullman; Georgia N. Kefallinos

(57) ABSTRACT

Described are overinflation and/or overventilation devices. The devices can include a body configured to attach to a resuscitation interface and a gas source, a subject metric input component disposed at the body, the subject metric input component configured to receive input specifying a metric associated with a resuscitation subject; and a volume control mechanism disposed within the body, the volume control mechanism configured to control a volume of gas provided by the gas source during a manual resuscitation that is communicated to the resuscitation interface based on the metric provided by the subject metric input component. Methods of using these devices are also included.

18 Claims, 9 Drawing Sheets

(51) Int. Cl.
*A61M 16/06* (2006.01)
*A61M 16/08* (2006.01)
*A61M 16/20* (2006.01)
*A61M 16/16* (2006.01)

(52) U.S. Cl.
CPC ........ *A61M 16/06* (2013.01); *A61M 16/0816* (2013.01); *A61M 16/20* (2013.01); *A61M 16/201* (2014.02); *A61M 16/161* (2014.02); A61M 2016/003 (2013.01); A61M 2016/0027 (2013.01); A61M 2202/0208 (2013.01); A61M 2205/3334 (2013.01); A61M 2205/50 (2013.01); A61M 2205/502 (2013.01); A61M 2205/581 (2013.01); A61M 2205/582 (2013.01); A61M 2205/583 (2013.01); A61M 2205/8206 (2013.01); A61M 2209/06 (2013.01); A61M 2230/432 (2013.01)

(56) References Cited

U.S. PATENT DOCUMENTS

| | | | | |
|---|---|---|---|---|
| 5,749,199 A * | 5/1998 | Allen | ............... | E04B 1/3555 52/837 |
| 5,944,013 A * | 8/1999 | Burch | ............... | A61M 16/0084 128/203.11 |
| 6,988,499 B2 * | 1/2006 | Holt | ............... | A61H 31/007 128/205.13 |
| 8,235,043 B2 * | 8/2012 | Halpern | ............ | A61M 16/0078 128/205.14 |
| 8,443,804 B2 * | 5/2013 | Lee | ............... | A61M 16/0075 128/203.28 |
| 9,586,015 B1 * | 3/2017 | Lindner | ............ | A61M 16/0078 |
| 2002/0117173 A1 * | 8/2002 | Lynn | ............... | A61M 16/0078 128/202.28 |
| 2003/0192547 A1 * | 10/2003 | Lurie | ............... | A61M 16/022 128/207.12 |
| 2007/0169780 A1 * | 7/2007 | Halpern | ............ | A61M 16/0084 128/205.15 |
| 2008/0053445 A1 * | 3/2008 | Kroupa | ............ | A61M 16/0084 128/205.23 |
| 2010/0036266 A1 * | 2/2010 | Myklebust | ........ | A61B 5/02444 600/500 |
| 2011/0284004 A1 * | 11/2011 | Silver | ............... | A61N 1/3925 128/205.13 |
| 2012/0302910 A1 * | 11/2012 | Freeman | ........... | A61M 16/0084 600/538 |
| 2013/0092166 A1 * | 4/2013 | Pearce | ............. | A61M 16/0084 128/205.14 |
| 2014/0275820 A1 * | 9/2014 | Varga | ............... | A61B 5/742 600/301 |

* cited by examiner

ADJUSTABLY CONTROLLING RESCUE OR ASSISTED BREATHS

CROSS REFERENCE TO RELATED APPLICATIONS

This application is a national phase entry of PCT/US2016/015803, filed Jan. 29, 2016, which claims the benefit of U.S. provisional patent application No. 62/109,181, filed Jan. 29, 2015, the entire disclosures each of which is incorporated herein by reference.

FIELD

This disclosure relates to devices, assemblies, and methods for adjustably controlling rescue or assisted breaths provided during manual resuscitation to prevent overinflation and/or overventilation.

BACKGROUND

A conventional manual resuscitator is a hand-held device commonly used to provide positive pressure ventilation to subjects who are not breathing or not breathing adequately. This manual resuscitator may also be referred to as a bag-valve-mask device (BVM), a bag-mask-ventilation (BMV) device, a self-inflating bag, or the proprietary name Ambu® bag. A manual resuscitator is a required part of resuscitation kits for trained professionals in out-of-hospital settings (e.g., ambulance crews) and is standard equipment found on a crash cart, in emergency rooms, or other critical care settings. Underscoring the frequency and prominence of manual resuscitator use in the United States, the American Heart Association (AHA) Guidelines for Cardiopulmonary Resuscitation and Emergency Cardiac Care recommend that "all healthcare providers should be familiar with the use of the bag-mask device." Manual resuscitators are also used within the hospital for temporary ventilation of patients dependent on mechanical ventilators when the mechanical ventilator needs to be examined for possible malfunction, or when ventilator-dependent patients are transported within the hospital. Two principal types of manual resuscitators exist. One version is self-filling with air, although additional oxygen ($O_2$) can be added but is not necessary for the device to function. The other principal type of manual resuscitator, known as flow-inflation type, is heavily used in non-emergent applications in the operating room to ventilate patients during anesthesia induction and recovery.

Under normal breathing, the lungs inflate under a slight vacuum when the chest wall muscles and diaphragm expand. This "pulls" the lungs open, causing air to enter the lungs to inflate under a gentle vacuum. When using a manual resuscitator, however, the lungs are force-inflated with pressurized air and/or oxygen. This inherently leads to risk of various complications. Complications are primarily related to overinflation and overventilation. Overinflation means that too much air is provided during individual resuscitative breaths. Overinflation can cause: (1) air to inflate the stomach (called gastric insufflation); (2) lung injury from over-stretching (called volutrauma); and/or (3) lung injury from over-pressurization (called barotrauma). Overventilation means that too many resuscitative breaths are provided per unit time. Overventilation can cause poor circulation in the body (e.g., poor venous return due to increased intrathoracic pressures).

Of the nearly 30 million visits to U.S. emergency departments by children, up to 5% may require some airway management or support of ventilation. This figure does not include the hundreds of thousands of cases in which children are manually ventilated during transport within and between institutions. Potential risks for complications related to overinflation and overventilation are magnified for children being resuscitated because the ventilation requirements can vary drastically based on body size. For example, dehydrated, critically ill children may be put at risk for cardiovascular collapse and cardiac arrest due to overinflation and/or overventilation.

SUMMARY

One aspect of the disclosure relates to a device configured to be disposed within a gas flow circuit of a manual resuscitator or manual respiration device in order to adjustably control rescue or assisted breaths (i.e., resuscitative breaths) provided during manual resuscitation to prevent overinflation and/or overventilation. Exemplary implementations provide an all-in-one device that prevents overinflation (e.g., by optimizing volume of individual resuscitative breaths) and overventilation (e.g., by keeping time for the next breath). The device may set an upper limit to the amount of gas (e.g., air and/or oxygen) in a resuscitative breath, decreasing the chance of overventilation and excessive thoracic pressures. In addition, a "metronome" feature may allow a healthcare provider to "keep time" with a flashing light (or other indication), to ventilate at a proper rate (e.g., to avoid acid-base disturbances in the blood).

Exemplary implementations of the device may be used in instances of manual ventilation and/or intubation in pre-hospital settings, and in instances of manual ventilation and many cases of intubation in hospital settings. The device may alleviate healthcare provider anxiety and/or provide performance improvement by reducing a lack of confidence with critically ill children by taking the "cognitive load" off the healthcare provider to focus on other tasks. Further, the device may help to simplify care and calm less experienced providers in a stressful resuscitation. In addition, the device may be an ideal training tool used on manikins to teach healthcare providers the optimal resuscitative breath volume and rate by pediatric age range.

According to some implementations, the device may be configured to be included in a manual resuscitator assembly. The manual resuscitator assembly may include one or more of a manual resuscitation gas source, a resuscitation interface, and/or other components.

The manual resuscitation gas source may be configured to provide gas for resuscitative breaths. The manual resuscitation gas source may include one or more of a resuscitation bag, an oxygen ($O_2$) source, a port for delivery of inhaled beta agonists or nebulized epinephrine for subjects with airway obstruction, and/or other gas sources. A resuscitation bag may include a soft bag element that can be squeezed to expel gas to the subject.

The resuscitation interface, or may also be referred to as a respiration interface, may be configured to form an interface between the subject and the manual resuscitator assembly such that gas expelled from the manual resuscitation gas source is provided to the lungs of the subject via the subject's airway (e.g., mouth and/or nose). The resuscitation interface may include one or more of a mask, an advanced airway, a supraglottic device, an extraglottic device, and/or other resuscitation interfaces.

The device may include a body having an inlet port and an outlet port. The inlet port may be configured to be attached to a gas flow circuit in fluid communication with the manual resuscitation gas source. The outlet port may be configured to be attached to the gas flow circuit in fluid communication with the resuscitation interface such that a portion of gas of a resuscitative breath provided during manual resuscitation is communicated from the manual resuscitation gas source via the inlet port to the resuscitation interface via the outlet port. In some implementations, one or both of the inlet port and/or the outlet port may comply with a standard for manual resuscitator parts such that the device is insertable into existing standard resuscitation equipment. For example, one or both of the inlet port and/or the outlet port may be compatible with the International Organization for Standardization (ISO) Code 5356-1 for anesthetic and respiratory equipment conical connectors.

The device may include a subject metric input component configured to receive input specifying a metric associated with a resuscitation subject. The metric associated with the subject may include one or more of a characteristic of the subject, a representation of a characteristic of the subject, and/or other metrics. Examples of characteristics of the subject may include one or more of a weight of the subject, a range of weights in which the subject's weight falls, a height of the subject, a range of heights in which the subject's height falls, an age of the subject, a range of ages in which the subject's age falls, a developmental stage of the subject (e.g., neonate, infant, child, adolescent, adult, and/or other developmental stages), body habitus (e.g., lean, average weight, overweight, obese), body mass index (BMI), and/or other characteristics.

The device may include a volume control mechanism configured to control a volume of a resuscitative breath provided during manual resuscitation that is communicated through the outlet port. In some implementations, the volume control mechanism may include a flow meter configured to determine a volume per resuscitative breath that is communicated through the outlet port. The volume control mechanism may include a valve configured to prevent, for a given resuscitative breath, any additional gas to flow out of the outlet in response to a volume of the given resuscitative breath that is communicated through the outlet port breaching a threshold. In some implementations, any excess volume of gas beyond the controlled volume that is introduced via the inlet port may be expelled from the device away from the gas flow circuit.

The volume of a resuscitative breath may be based on a metric received by the subject metric input component. That is, a threshold volume that is expelled via the outlet port per resuscitative breath may be determined based on the metric. The controlled volume for a given resuscitative breath may fall between an optimum volume and a maximum volume associated with the metric received by the subject metric input component. In implementations in which the metric includes the weight of the subject, or the weight of the subject can be inferred from the metric, the optimum volume per resuscitative breath may be approximately 6 mL of gas per 1 kg of body weight, while the maximum volume per resuscitative breath may be approximately 8 mL/kg.

The device may include a timing device configured to provide an indication to a healthcare provider performing manual resuscitation to convey a time period between resuscitative breaths. The indication may include feedback that is one or more of visual, audio, or haptic. In some implementations, the time period between resuscitative breaths may be determined such that a rate of resuscitative breaths at the controlled volume provided during manual resuscitation will result in a gas pressure threshold at the resuscitation interface remaining unbreached. The pressure of the gas for various breath volumes and rates may be determined though calibration and/or direct measurement using a pressure sensor included in the device.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION

Figure 1:
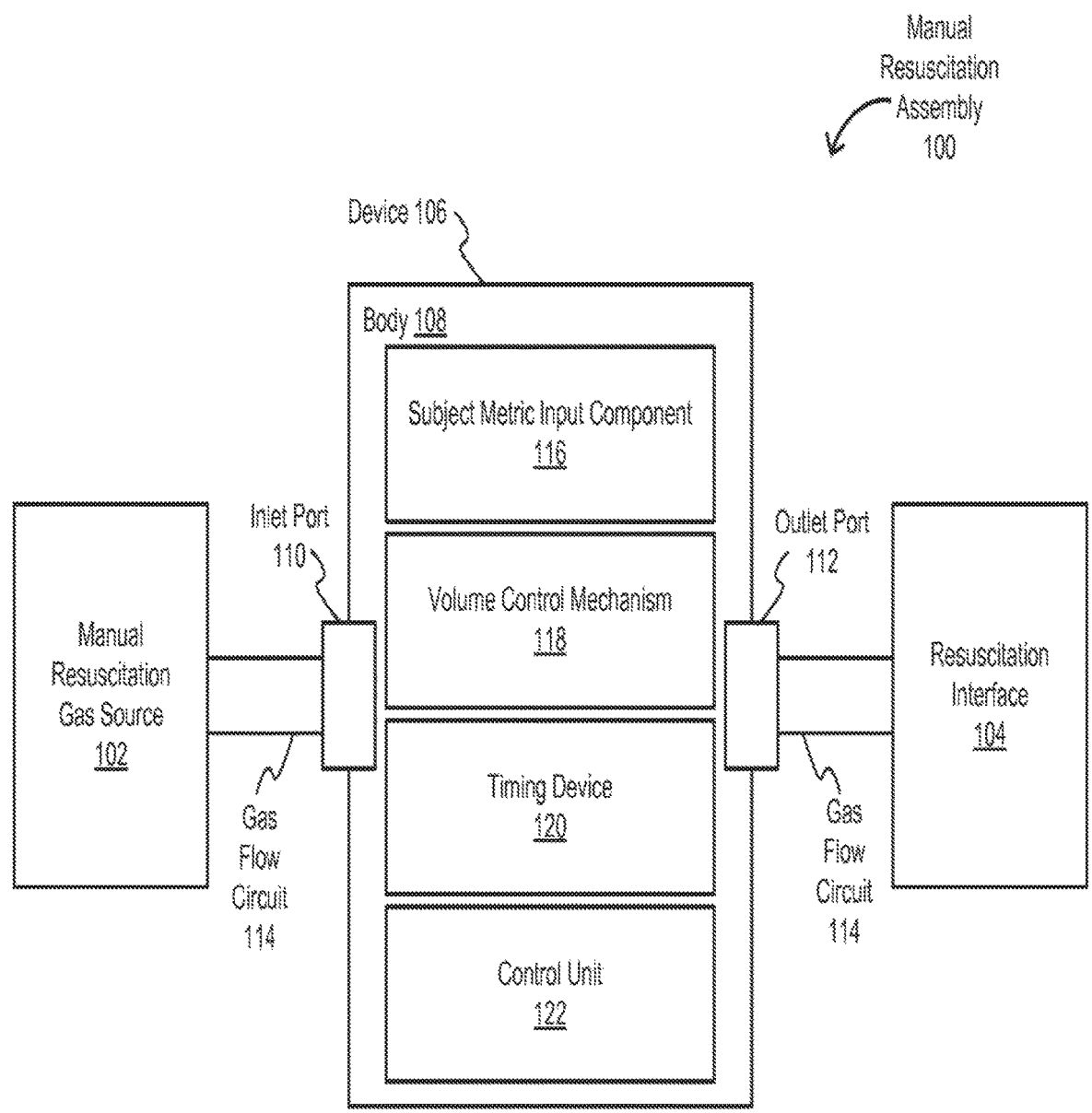
FIG. 1 illustrates a manual resuscitator assembly configured for adjustably controlling rescue or assisted breaths provided during manual resuscitation to prevent overinflation and/or overventilation, in accordance with one or more implementations.

FIG. 1 illustrates a manual resuscitator assembly 100 configured for adjustably controlling rescue or assisted breaths (i.e., resuscitative breaths) provided during manual resuscitation to prevent overinflation and/or overventilation, in accordance with one or more implementations. The manual resuscitator assembly 100 may include one or more of a manual resuscitation gas source 102, a resuscitation interface 104, a device 106, and/or other components.

The manual resuscitation gas source 102 may be configured to provide gas for resuscitative breaths. The gas may include one or more of air, a pure gas (e.g., oxygen ($O_2$)), a medication, and/or other gases. The manual resuscitation gas source 102 may include one or more of a resuscitation bag (e.g., abu bag), an oxygen ($O_2$) source, and/or other gas sources. A resuscitation bag may include a soft bag element that can be squeezed to expel gas to the subject. The resuscitation bag may include a valve to prevent backflow into the bag itself (e.g., to prevent patient deprivation and/or bag contamination). The oxygen source may include a bottle of compressed oxygen that is used to provide pure oxygen or to supplement air with oxygen for resuscitative breaths.

In some embodiments, manual resuscitation gas source 102 may be sized for a particular sized human. In other embodiments, a standard sized manual resuscitation gas source can be used that is regulated by the devices descried herein.

The resuscitation interface 104 may be configured to form an interface between the subject and manual resuscitator assembly 100 such that gas expelled from manual resuscitation gas source 102 is provided to the lungs of the subject via the subject's airway (e.g., mouth and/or nose). The resuscitation interface may include one or more of a mask, an advanced airway, a supraglottic device, an extraglottic device, and/or other resuscitation interfaces. The mask may include a flexible mask to seal over the subject's face or a portion thereof. The advanced airway may include an endotracheal tube, a supraglottic device, an extraglottic device, and/or other advanced airways.

The device 106 may be configured to adjustably control resuscitative breaths provided during manual resuscitation to prevent overinflation and/or overventilation. The device 106 may include a body 108 having an inlet port 110 and an outlet port 112. The body 108 may be configured to enclose and/or support one or more components of device 106. The body 108 may be formed of a ridged or semi-ridged material such as one or more of a plastic, a metal, and/or other materials.

The inlet port 110 may be configured to be attached to a gas flow circuit 114 in fluid communication with the manual resuscitation gas source 102. The outlet port 112 may be configured to be attached to gas flow circuit 114 in fluid communication with resuscitation interface 104 such that a portion of gas of a resuscitative breath provided during manual resuscitation is communicated from manual resuscitation gas source 102 via inlet port 110 to resuscitation interface 104 via outlet port 112. In some implementations, one or both of inlet port 110 and/or outlet port 112 may comply with a standard for manual resuscitator parts such that device 106 is insertable into existing standard resuscitation equipment. For example, one or both of inlet port 110 and/or outlet port 112 may be compatible with the International Organization for Standardization (ISO) Code 5356-1 for anesthetic and respiratory equipment conical connectors. Other connections can include pressure fit connections, snapping connections, compression fittings, luer-locking fittings, and the like.

The device 106 may include a subject metric input component 116. The subject metric input component 116 may be disposed at body 108. The subject metric input component 116 may be configured to receive input specifying a metric associated with a resuscitation subject. The subject metric input component 116 may include a mechanical component and/or an electronic component. In various implementations, subject metric input component 116 may include one or more of a dial, a keypad, a button, a slider, and/or other input components. The metric associated with the subject may include one or more of a characteristic of the subject, a representation of a characteristic of the subject, and/or other metrics. Examples of characteristics of the subject may include one or more of a weight of the subject, a range of weights in which the subject's weight falls, a height of the subject, body habitus, BMI, a range of heights in which the subject's height falls, an age of the subject, a range of ages in which the subject's age falls, a developmental stage of the subject (e.g., neonate, infant, child, adolescent, adult, and/or other developmental stages), and/or other characteristics. The representation of a characteristic of the subject may include one or more of a pictorial representation, a graphical representation, an alphanumerical representation, color-coding, and/or other representations. By way of non-limiting example, according to some implementations, representations of a characteristic of the subject may include one or more of a star rating, a numerical rating, varying shapes, varying raised or depressed portions (e.g., bumps or dimples) silhouettes of varying body sizes or ages, a sliding scale, color-coding representing height and/or weight, and/or other representations.

The device 106 may include a volume control mechanism 118. The volume control mechanism 118 may be disposed within body 108. The volume control mechanism 118 may be configured to control a volume of a resuscitative breath provided during manual resuscitation that is communicated through outlet port 112. In some implementations, volume control mechanism 118 may include a flow meter configured to determine a volume per resuscitative breath that is communicated through outlet port 112. The flow meter may include one or more of a mechanical flow meter, a pressure-based meter, and/or other flow meters.

A mechanical flow meter may directly measure volumetric flow by constantly filling and emptying known volumes (e.g., space between gear teeth, piston cylinders) and/or other mechanical techniques. Examples of mechanical flow meters may include one or more of a piston meter or rotary piston, a gear meter (e.g., an oval gear meter, a helical gear meter, a nutating gear meter, and/or other gear meter), a variable area meter, a turbine flow meter, a Woltmann meter, a single jet meter, a paddle wheel meter, a multiple jet meter, a Pelton wheel, a current meter, and/or other mechanical flow meters.

A pressure-based meter may rely on Bernoulli's principle, either by measuring the differential pressure within a constriction, or by measuring static and stagnation pressures to derive the dynamic pressure. Examples of pressure-based meters may include one or more of a venturi meter, an orifice plate, a Dall tube, a pitot tube, a multi-hole pressure probe, a cone meter, and/or other pressure-based meters.

The volume control mechanism 118 may include a valve configured to prevent, for a given resuscitative breath, any additional gas to flow out of outlet 112 in response to a volume of the given resuscitative breath that is communicated through outlet port 112 breaching a threshold. In some implementations, any excess volume of gas beyond the controlled volume that is introduced via inlet port 110 may be expelled from device 106 away from gas flow circuit 114.

The volume control mechanism 118 may include an indicator that conveys what portion or fraction of the controlled volume has already been expelled by outlet port 112 during administration of a resuscitative breath. For example, the indicator may convey that about 75% (or any other portion or fraction) of a breath has been expelled. Such an indication may assist a healthcare provider operating manual resuscitation assembly 100 in providing resuscitative breaths at a desired rate at a steady pressure. The indicator may include one or more of a visual indicator (e.g., a dial, a gauge, a digital display, a series of lights or LEDs, and/or other visual indicators), an audio indicator (e.g., a tone, pulse, bell, and/or other audio indicators), a haptic indicator (e.g., a vibrator), and/or other indicators.

The volume of a resuscitative breath may be based on a metric received by subject metric input component 116. That is, a threshold volume that is expelled via outlet port 112 per resuscitative breath may be determined based on the metric. The controlled volume for a given resuscitative breath may fall between an optimum volume and a maximum volume associated with the metric received by subject metric input component 116. In implementations in which the metric includes the weight of the subject, or the weight of the subject can be inferred from the metric, the optimum volume per resuscitative breath may be approximately 6 mL of gas per 1 kg of body weight, while the maximum volume per resuscitative breath may be approximately 8 mL/kg. According to some implementations, there may be a discrete number of settings for metrics inputted via subject metric input component 110. Individual settings may correspond to different controlled volumes for resuscitative breaths. Where there are eight settings, they may include the values outlined below in TABLES 1 and 2. The values presented in TABLES 1 and 2 should not be construed as limiting as other values, ranges, metrics, settings, and number of settings are contemplated and are within the scope of the disclosure.

TABLE 1

Exemplary optimum volumes per resuscitative breath.

| Setting | Subject's weight | Volume per breath |
|---|---|---|
| Newborn | 3-5 kg | 32 mL/breath |
| Infant | 6-9 kg | 64 mL/breath |
| Toddler | 10-14 kg | 96 mL/breath |
| Child | 15-18 kg | 136 mL/breath |
| Child | 19-29 kg | 176 mL/breath |
| Child | 30-36 kg | 256 mL/breath |
| Child | 37-49 kg | 336 mL/breath |
| Child/Adolescent | 50+ kg | 450 mL/breath |

TABLE 2

Exemplary optimum volumes per resuscitative breath.

| Setting | Subject's weight | Volume per breath |
|---|---|---|
| Newborn | 3-5 kg | 40 mL/breath |
| Infant | 6-9 kg | 72 mL/breath |
| Toddler | 10-14 kg | 112 mL/breath |
| Child | 15-18 kg | 144 mL/breath |
| Child | 19-29 kg | 232 mL/breath |
| Child | 30-36 kg | 288 mL/breath |
| Child | 37-49 kg | 392 mL/breath |
| Child/Adolescent | 50+ kg | 450 mL/breath |

The device 106 may include a timing device 120. The timing device 120 may be disposed on and/or within body 108. The timing device 120 may be configured to provide an indication to a healthcare provider performing manual resuscitation to convey a time period between resuscitative breaths. The indication may include feedback that is one or more of visual, audio, or haptic. By way of non-limiting example, device 106 may include a light metronome, activated by pulling a strip (e.g., to put the battery in physical contact with a light source conduit). When the light is flashing, the healthcare provider will squeeze on the bag, delivering a resuscitative breath. The light may flash over a period of time (e.g., 1 sec for adults, 1.5 seconds for children, and/or other time periods) and the interval between flashes may determine the respiratory rate (e.g., "flashes per min" may translate to breaths/min). The time period between resuscitative breaths may be determined based on a metric received by subject metric input component 116.

In some implementations, the time period between resuscitative breaths may be determined such that a rate of resuscitative breaths at the controlled volume provided during manual resuscitation will result in a gas pressure threshold at the resuscitation interface remaining unbreached. By way of non-limiting illustration, if a 360 mL resuscitative breath is being administered over 1.25 seconds, the resulting rate of gas flow out of outlet 112 may cause the pressure of the gas being expelled from resuscitation interface 104 to not exceed a safe pressure level. The pressure of the gas for various breath volumes and rates may be determined though calibration and/or direct measurement using a pressure sensor (not depicted) included in device 106.

The device 106 may include a control unit 122. The control unit 122 may include one or more processors configured to execute computer readable instructions. The computer program instructions may control one or more components of manual resuscitation assembly 100, coordinate operation of one or more components of manual resuscitation assembly 100, and/or provide some or all functionality attributed herein to manual resuscitation assembly 100 and/or device 106. The processor(s) may include one or more of a digital processor, an analog processor, a digital circuit designed to process information, an analog circuit designed to process information, a state machine, and/or other mechanisms for electronically processing information. The processor(s) may be configured to execute computer readable instructions by software; hardware; firmware; some combination of software, hardware, and/or firmware; and/or other mechanisms for configuring processing capabilities on the processor(s).

Figure 2A:
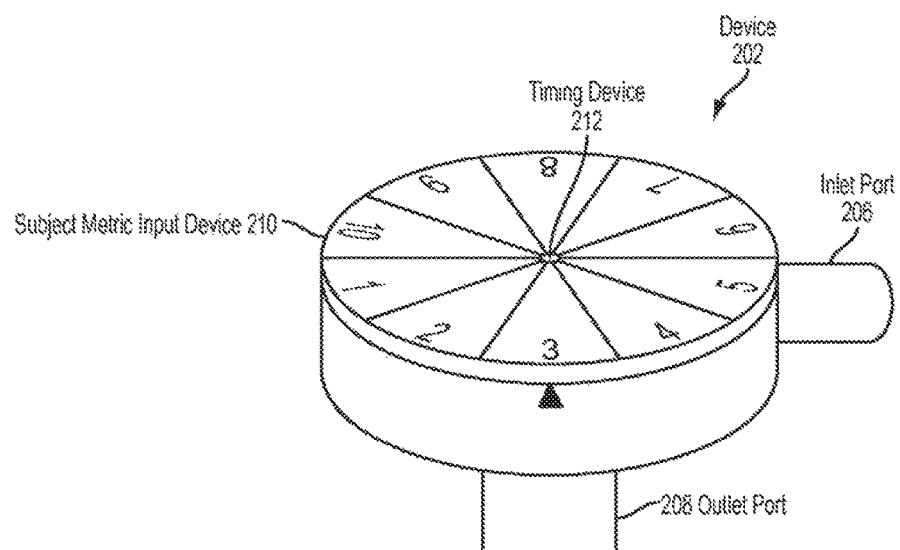
FIG. 2A illustrates an exemplary implementation of a device configured to be disposed within a gas flow circuit of a manual resuscitator in order to adjustably control rescue or assisted breaths provided during manual resuscitation to prevent overinflation and/or overventilation.
Figure 2B:
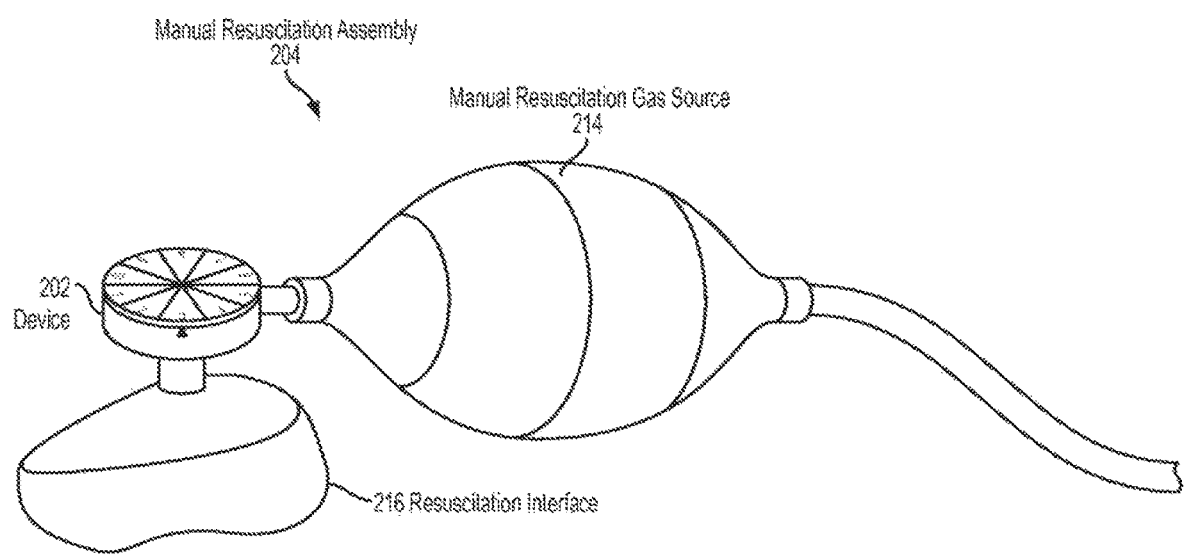
FIG. 2B illustrates an exemplary implementation of a manual resuscitator assembly configured for adjustably controlling rescue or assisted breaths provided during manual resuscitation to prevent overinflation and/or overventilation.

FIG. 2A illustrates an exemplary implementation of a device 202, and FIG. 2B illustrates an exemplary implementation of a manual resuscitator assembly 204 (which includes device 202) configured for adjustably controlling rescue or assisted breaths provided during manual resuscitation to prevent overinflation and/or overventilation. The device 202 may include an inlet port 206, an outlet port 208, a subject metric input component 210, a timing device 212, and/or other components. One or more components of device 202 may be the same as or similar to one or more components of device 106 shown in FIG. 1. The inlet port 206 may be configured to removably or permanently attach in fluid communication with a manual resuscitation gas source 214 (e.g., a resuscitation bag). The outlet port 208 may be configured to removably or permanently attach in fluid communication with a resuscitation interface 216 (e.g., a resuscitation mask). The subject metric input component 210 may be configured to receive input regarding a metric associated with a subject (e.g., by twisting a knob or dial). The timing device 212 may be configured to provide an indication (e.g., a blinking light) to a healthcare provider performing manual resuscitation to convey a time period between resuscitative breaths. The device 202 and manual resuscitation assembly 204 shown in FIGS. 2A and/or 2B are not intended to be limiting as other configurations are contemplated and are within the scope of the disclosure.

Figure 3:
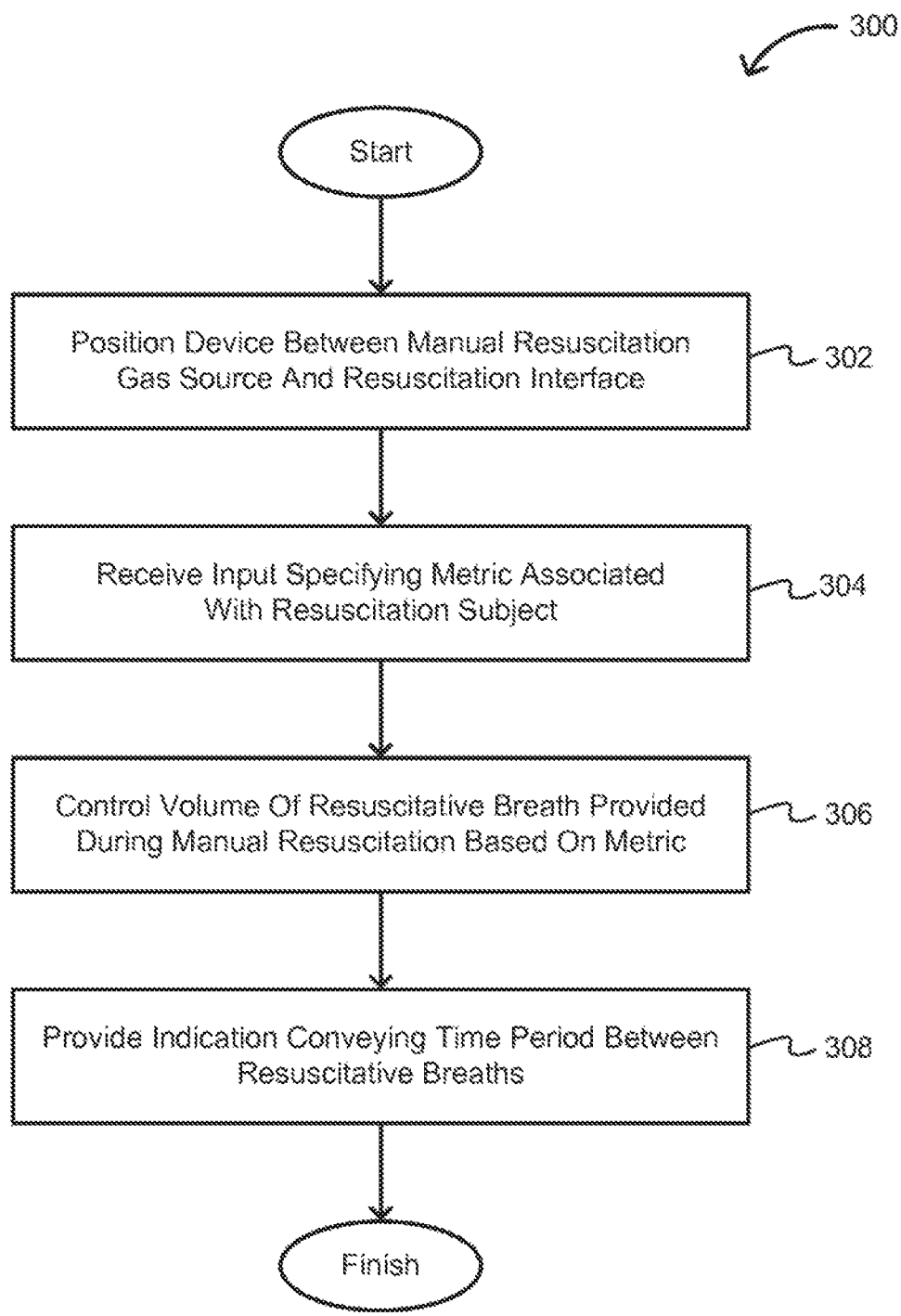
FIG. 3 illustrates a method for manual resuscitator assembly operation involving adjustably controlling rescue or assisted breaths provided during manual resuscitation to prevent overinflation and/or overventilation, in accordance with one or more implementations.

FIG. 3 illustrates a method 300 for manual resuscitator assembly operation involving adjustably controlling resuscitative breaths provided during manual resuscitation to prevent overinflation and/or overventilation, in accordance with one or more implementations. The steps of method 300 presented below are intended to be illustrative. In some implementations, method 300 may be accomplished with one or more additional steps not described, and/or without one or more of the steps discussed. Additionally, the order in which the steps of method 300 are illustrated in FIG. 3 and described below is not intended to be limiting.

At a step 302, a device (e.g., device 106) may be positioned between a manual resuscitation gas source (e.g., manual resuscitation gas source 102) and a resuscitation interface (e.g., resuscitation interface). The device may be positioned by an inlet port (e.g., inlet port 110) of the device being attached to the manual resuscitation gas source and an outlet port (e.g., outlet port 112) of the device being attached to the resuscitation interface such that a portion of gas of a resuscitative breath provided during manual resuscitation is communicated from the manual resuscitation gas source via the inlet port to the resuscitation interface via the outlet port.

At a step 304, input may be received specifying a metric associated with a resuscitation subject. The input may be received via a subject metric input component (e.g., subject metric input component 116) disposed at the device.

At a step 306, a volume may be controlled of the portion of gas of the resuscitative breath provided during manual resuscitation that is communicated through the outlet port based on the metric received by the subject metric input component. Step 306 may be performed by volume control mechanism 118, in accordance with one or more implementations.

At a step 308, an indication may be provided to convey a time period between resuscitative breaths. The indication may be provided for presentation to a healthcare provider performing manual resuscitation. The indication may be provided by timing device 120.

Figure 4:
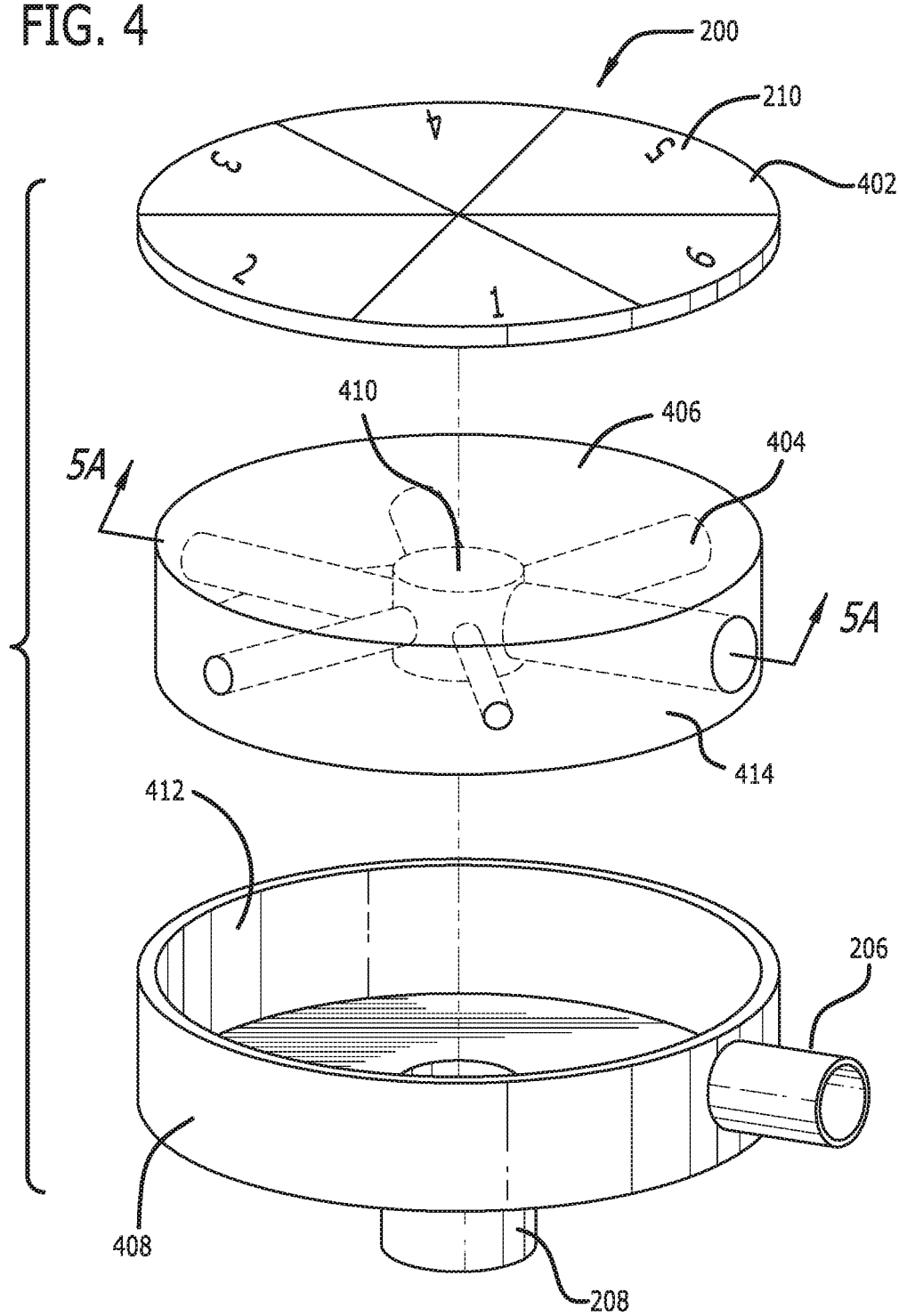
FIG. 4 illustrates an exploded view of a non-limiting device as described herein.
Figure 5A:
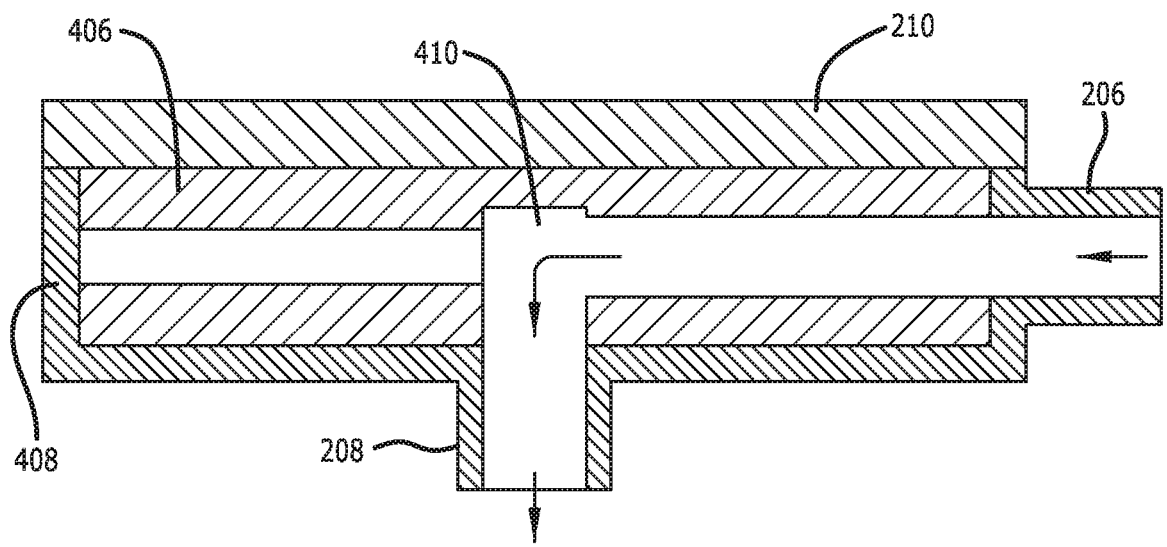
FIG. 5A is a cross-sectional view of the device of FIG. 4 in a first configuration.
Figure 5B:
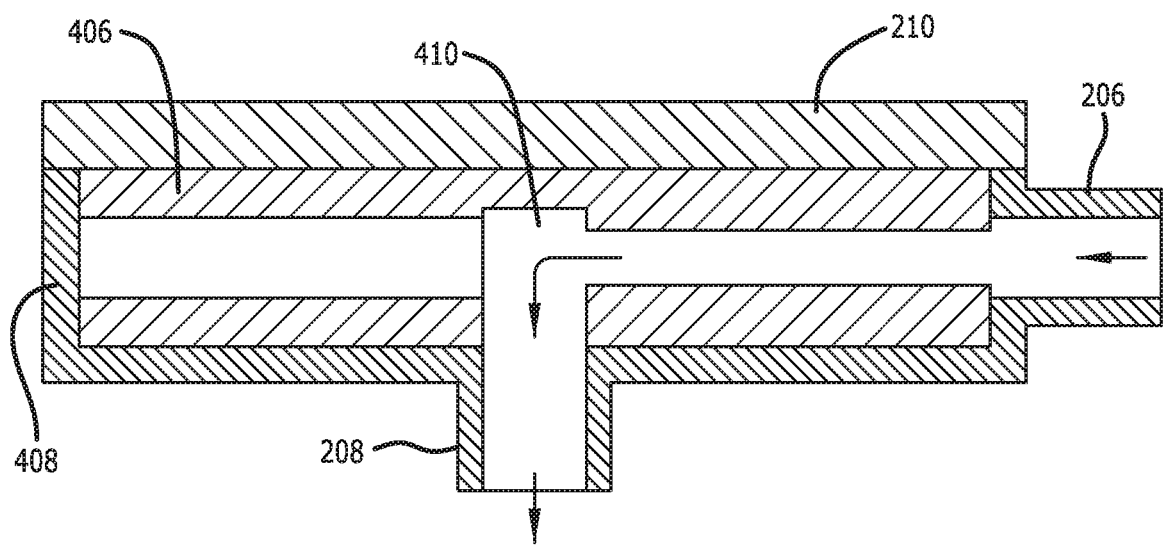
FIG. 5B is a cross-sectional view of the device of FIG. 4 in a second configuration.

FIGS. 4 and 5A and 5B illustrate an embodiment of a device 200. Device 200 includes a volume control mechanism comprising a subject metric input device 210 to select or "dial" an appropriate setting for a particular patient being treated. Each quadrant, e.g., quadrant 402 can represent and be associated with a particular diameter feed line, e.g., feed line 404 that is integrated into selection disk 406. In FIG. 4, subject metric input device 210 includes six quadrants and hence six volume control settings. In some embodiments, other volume control mechanisms can include more than six quadrants such as, but not limited to, 7, 8, 9, 10, 11, 12, 13, fourteen, fifteen, sixteen, seventeen, eighteen nineteen, twenty or more quadrants. In still other embodiments, other volume control mechanisms can include fewer than six quadrants such as 2, 3, 4, or 5 quadrants. Each quadrant can be labeled using any combination of numbers, letters, symbols, or any other character used to indicate a particular feature.

Selection disk 406 can be spun using the disk itself or by actuating attached subject metric input device 210. When volume control mechanism 118 is dialed or spun to a particular setting that quadrant's feed line enters into fluid communication with inlet port 206 which is in operable attachment to housing 408. Depending on the diameter of a particular feed line, more or less air volume can be pumped and/or fed through device 200.

In some embodiments, even the smallest diameter feed line can provide at least about 15 cc of air to a patient. In other embodiments, even the smallest diameter feed line can provide at least about 30 cc of air to a patient. In still other embodiments, even the smallest diameter feed line can provide at least about 45 cc of air to a patient. Each device described herein can provide at least about 15 cc, at least about 30 cc, or at least about 45 cc of air to a patient. In some embodiments, devices can include a fail-safe airway that can prevent patient airflow from falling below these values and potentially harming a patient.

Each feed line 404 terminates at hub 410. Hub 410 is in fluid communication with outlet port 208 as illustrated in FIGS. 5A and 5B which can be associated with resuscitation interface 216. Further, each feed line that is not in the selected position is sealed against inside wall 412 of housing 408 to prevent escape of air though that particular feed line. In some embodiment, inside wall 412 can include a coating of a lubricious material to assist in spinning. In other embodiments, inside wall 412 can include a coating of a material that can assist in sealing inside wall against outside wall 414 of selection disk.

Figure 6:
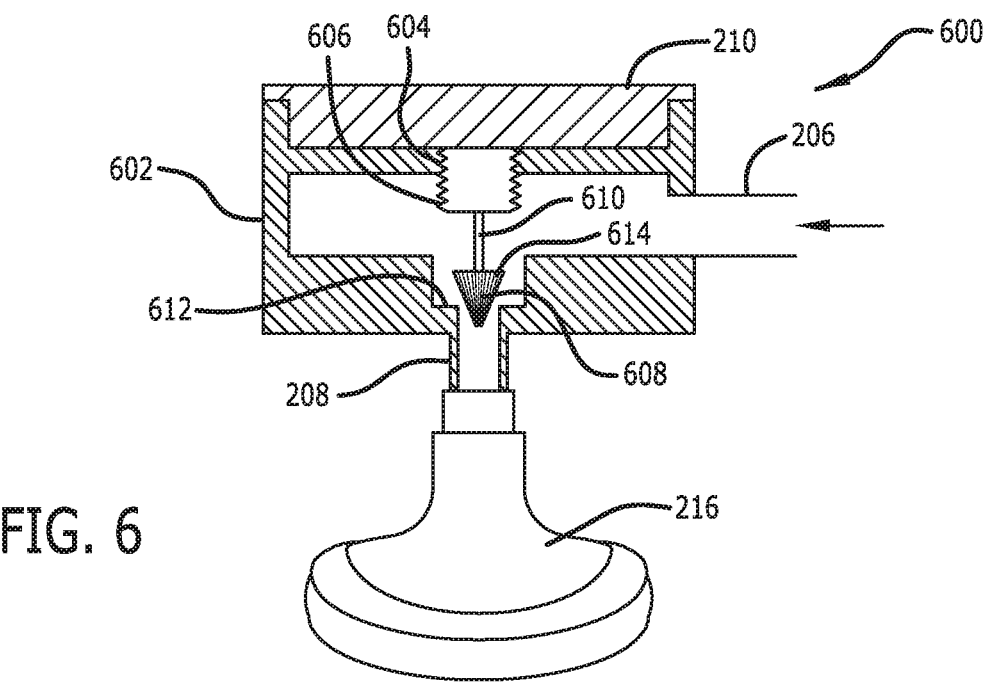
FIG. 6 is a cross-sectional view of a non-limiting example of another device in a first configuration.
Figure 7:
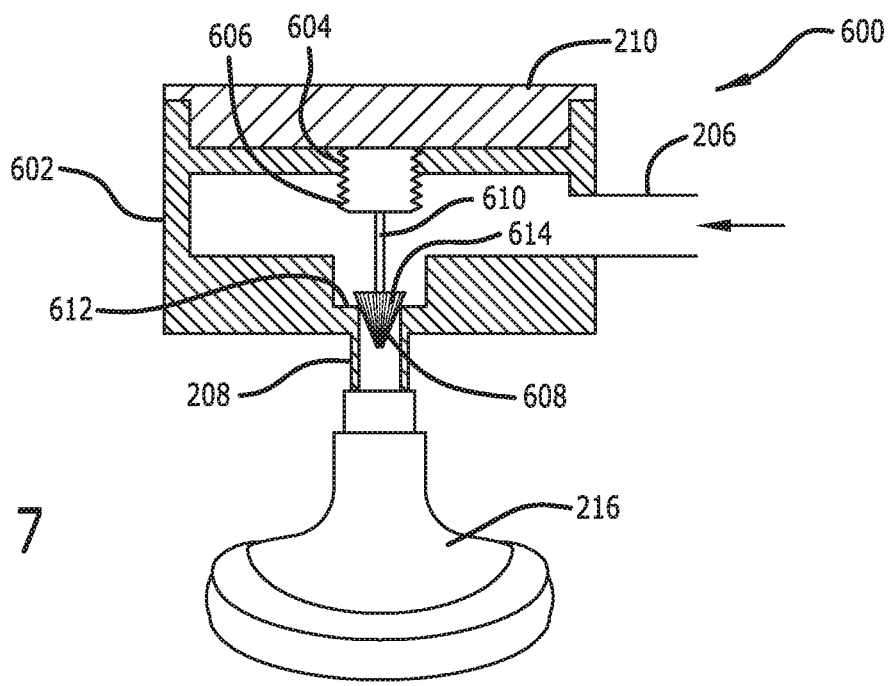
FIG. 7 is a cross-sectional view of the device of FIG. 6 in a second configuration.

FIGS. 6 and 7 illustrate another embodiment of a device, device 600. Here, subject metric input device 210 sits atop a housing 602. Housing 602 includes a threaded portion 604 that accepts a complimentary threaded portion 606 associated with subject metric input device 210. In one embodiment, as subject metric input device 210 is dialed to larger quadrant values, complimentary threaded portion 606 is further advanced through threaded portion 604.

In one embodiment, a stopper 608 is attached to complimentary threaded portion 606 through interface 610. In some embodiments, stopper 608 can be attached directly to complimentary threaded portion 606 and interface 610 is not needed. As complimentary threaded portion 606 is advanced further through threaded portion 604, stopper 608 can interface with lip 612 associated with outlet port 208. As stopper 608 comes closer and closer to lip 612, less and less air can be allowed to reach outlet port 208.

In some embodiments, stopper 608 can have a conical shape. However, other shapes can be used, such as but not limited to rectangular, cylindrical, spherical, triangular, and other rectilinear shapes. In some embodiments, stopper 608 can include one or more by-pass channels 614 on the surface of stopper 608 so that a small amount of air can still pass the stopper if the stopper is fully engaged with lip 612 (as illustrated in FIG. 7).

Device 600 can be configured to include open and close and aperture such as an iris that at reduce and increase flow depending on the size of the aperture. For example, as subject metric input device 210 is used to select a setting, interface 610 can open and close an aperture that resides between inlet port 206 and outlet port 208. In other embodiments, an aperture can be opened and closed electronically instead of using tooling such as interface 610.

In some embodiments, the device can include one or more sensor that can aid in controlling the aperture. In such an embodiment, if a sensor such as a flow sponsor detects that flow is too might for a given setting, a processor in communication with the sensor can reduce the size of the aperture. Likewise, if a sensor such as a flow sponsor detects that flow is too low for a given setting, a processor in communication with the sensor can increase the size of the aperture. Other sensors that can be used include gas sensors, temperature sensors, resistivity sensors, humidity sensors, pressure sensors, and the like. Combinations of sensors can also be used.

In some embodiments, the device illustrated in FIGS. 4-7 can function electronically. In some embodiments, dialing subject metric input device 210 can effectuate a processor to turn hub 406, raise or lower stopper 608, or even open or close an aperture. The processor can be powered by a battery or any other external power source.

In some embodiments, a battery can be any standard sized battery. Standard size batteries can include, but are not limited to round, cylindrical batteries such as AA, AAA, AAAA, C, D, and button cell (such as lithium button), coin cell, and non-round batteries such as 4.5V box and 9V box batteries, and the like. Further button cell or coin cell batteries can be used. Batteries can be removed as needed to clean and/or sterilize the device. In still other embodiments, proprietary battery packs can be provided to fit a particular slot or opening on or in a device.

In some embodiments, batteries used can be rechargeable. In some embodiments, devices described herein that can utilize one or more rechargeable batteries can be provided with a charging station. A charging station can charge one or more batteries, a battery pack, of the device itself with the batteries inside.

Figure 8:
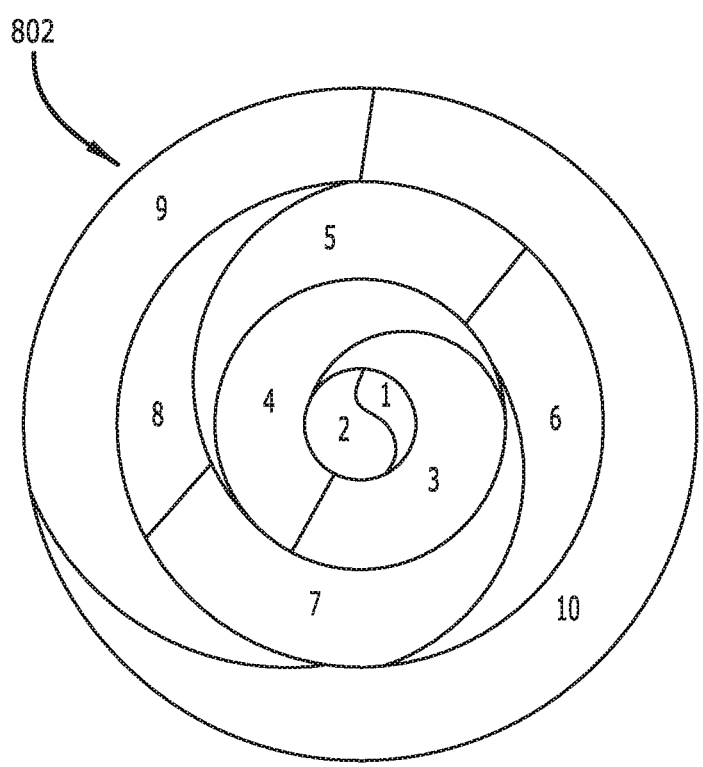
FIG. 8 illustrates a spiral dial used to regulate air flow exiting a device through an outlet port.

FIG. 8 illustrates another embodiment of a volume control mechanism 118. Spiral dial 802 can be mounted below a subject metric input device such as subject metric input device 210. Spiral dial 802 may not be drawn to scale. Spiral may be similar to a corkscrew. As subject metric input device 210 is moved to increasing quadrants, spiral dial 802 can allow air entering air inlet port 206 to travel through larger portions of spiral dial 802. Each different spiral portion can increase or decrease the flow though the device and out of outlet port 208. In some embodiments, quadrant labeled "1" on subject metric input device 210 can correspond to spiral portion of spiral dial 802 labeled "1;" quadrant labeled "2" on subject metric input device 210 can correspond to spiral portion labeled "2;" quadrant labeled "3" on subject metric input device 210 can correspond to spiral portion labeled "3;" quadrant labeled "4" on subject metric input device 210 can correspond to spiral portion labeled "4;" quadrant labeled "5" on subject metric input device 210 can correspond to spiral portion labeled "5;" quadrant labeled "6" on subject metric input device 210 can correspond to spiral portion labeled "6;" quadrant labeled "7" on subject metric input device 210 can correspond to spiral portion labeled "7;" quadrant labeled "8" on subject metric input device 210 can correspond to spiral portion labeled "8;" quadrant labeled "9" on subject metric input device 210 can correspond to spiral portion labeled "9;" and quadrant labeled "10" on subject metric input device 210 can correspond to spiral portion labeled "10." As stated previously, in some embodiments, other volume control mechanisms can include more than ten quadrants. In still other embodiments, other volume control mechanisms can include fewer than ten quadrants. Likewise, spiral dial 802 can include more or less than ten portions.

In some embodiments, devices herein can be preventative in nature. In such embodiments, subject metric input device 210 can moved to a desired position wherein a valve is used to vent excess airflow that is not desired. This configuration can aid in preventing injury to a patient. In some embodiments, the valve can be a flutter valve or other venting valve.

In one embodiment, a venting valve can be any type of safety value. In some embodiments, a safety valve can be a pop-off style safety valve or a flutter valve as descried above. Such a valve stays sealed until a pressure or flow threshold is reached wherein the valve includes a portion that "pops off" to vent excess pressure or flow. Other safety valves can also be used.

Figure 9:
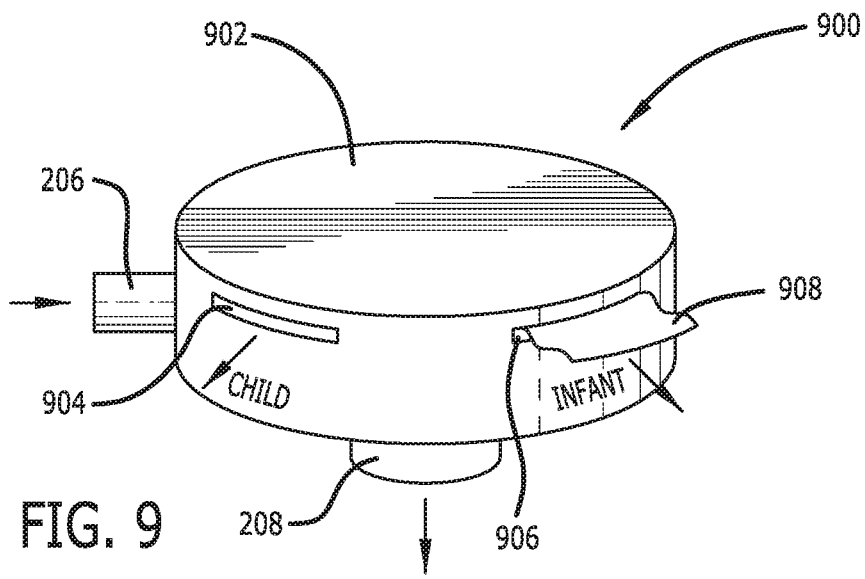
FIG. 9 illustrates a device with an audible bleed orifice and a visual bleed orifice. In some embodiments, a device only includes an audible bleed orifice. In other embodiments, a device only includes a visual bleed orifice.

A feature that can be added to devices described herein are audible and/or visible indicators that alert that a particular setting(s) is functioning. As illustrated in FIG. 9, device 900 includes a housing 902, an inlet port 206, and an outlet port 208. Device 900 can be equipped with a volume control mechanism 118, subject metric input device 210, or any other systems/devices described herein. Device 900 can also include one or more bleed orifices that can assist in displaying device functionality.

In one embodiment, audible bleed orifice 904 can allow a small amount of air through the orifice thereby emitting a noise which indicates device functionality. Audible bleed orifice 904 can assume any shape that allows it to emit a noise when air is passing through it. In one embodiment, audible bleed orifice 904 can have a slotted shape.

Further, audible bleed orifice 904 can be used in conjunction with a venting valve to indicate that too much airflow is being provided and that excess air is being vented from the device.

In another embodiment, visual bleed orifice 906 can allow a small amount of air through the orifice thereby moving flag 908 which waves and indicates device functionality. Visual bleed orifice 906 can assume any shape that allows it to move flag 908 when air is passing through it. In one embodiment, visual bleed orifice 906 can have a slotted shape. In some embodiments, flag 908 can be of a color that allows a user to freely see when it is moving. Exemplary colors can be red, green, yellow, orange, or the like.

Further, visual bleed orifice 906 can be used in conjunction with a venting valve to indicate that too much airflow is being provided and that excess air is being vented from the device.

Figure 10:
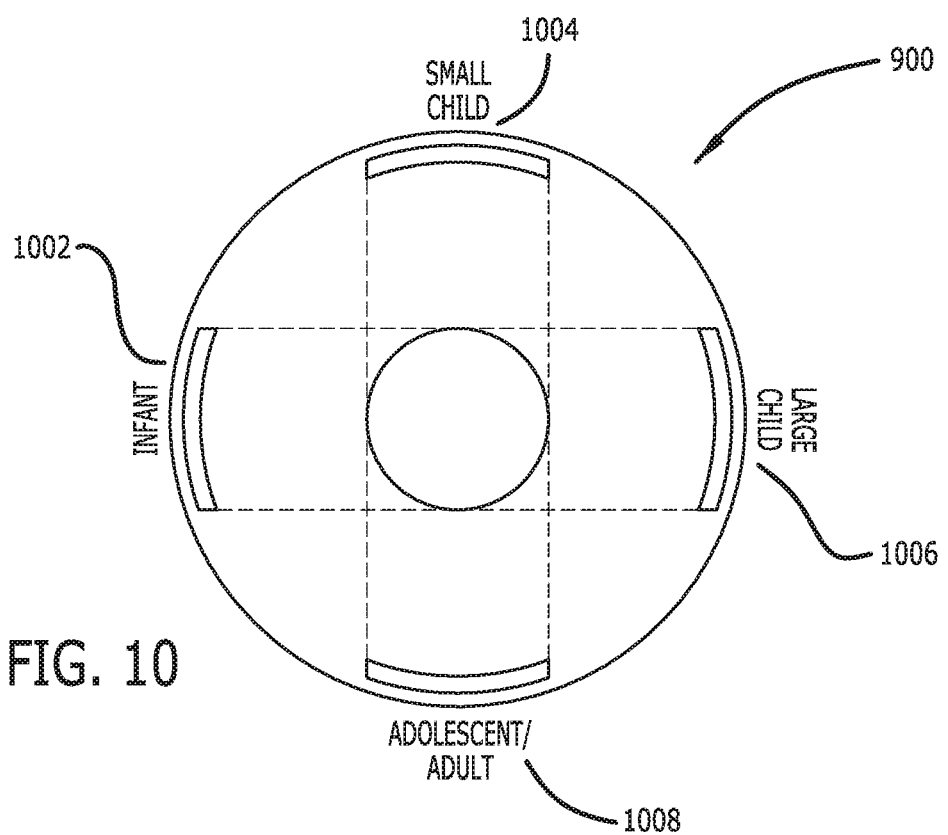
FIG. 10 illustrates a device that includes an audible and or a visual bleed orifice in conjunction with four user selectable settings.

FIG. 10 illustrates another embodiment of a device 1000. Device 1000 includes four dial locations, location 1002, location 1004, location 1006 and location 1008. In one embodiment, location 1002 may be for an infant, location 1004 may be for a small child, location 1006 may be for a large child, and location 1008 may be for an adolescent/adult. Other configurations are also possible and more or less than four locations are possible. Each of location 1002, location 1004, location 1006 and location 1008 can include a bleed orifice that provides audible or visual indication and/or feedback. Such configurations allow a user to visually or audibly know that the device is functioning properly during use. In some embodiments, each location can active a particular venting valve that can prevent excess airflow from being delivered to the patient.

In other embodiments, in addition to or in place of a visual or audible bleed orifice, device 106 or any device described herein can include a safety value to vent express pressure or flow. In one embodiment, each setting on a device can include a safety value set to a particular pressure or flow based on a particular setting.

Figure 11:
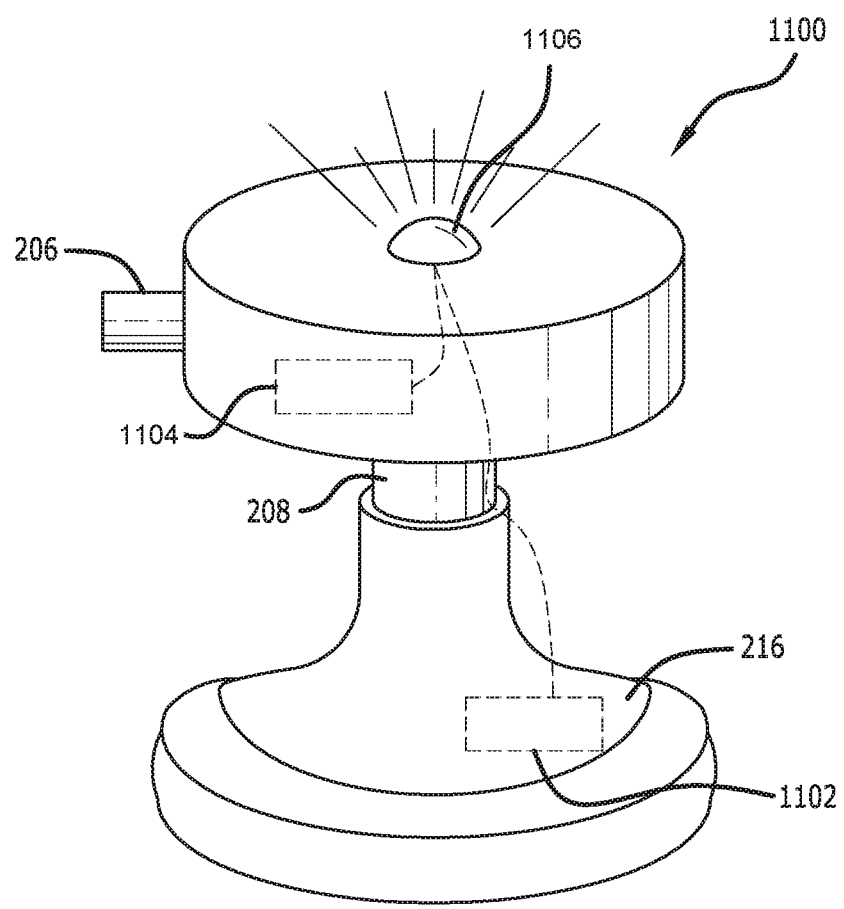
FIG. 11 illustrates a device including a sensing system in conjunction with other features described herein.

FIG. 11 illustrates another feature that can be added to devices described herein. Device 1100, which can include any set of features or combination of features described herein, further includes a sensing system. Sensing system includes at least one sensor, a processor, and an indication feature. Device 1100 includes sensor 1102 associated with resuscitation interface 216. Alternatively or additionally, device 1100 can include sensor 1102 associated with the device itself. Device 1100 can include more than one sensor. In some embodiments, device 1100 can include 2, 3, 4, 5, 6, 7, 8, 9, 10, 11, 12, or more sensors. Sensors can be associated with resuscitation interface 216, volume control mechanism 118, subject metric input device 210, inlet port 206, outlet port 208, gas source 214, combinations thereof, or the like.

Device 1100 can include an electronics system 1104 including a processor that accepts data from sensors and outputs data to indication feature 1106. Communication between sensors, electronics system 1104, and indication feature 1106 can be through a wired configuration, a wireless configuration, or a combination thereof.

Indication feature 1106 can be an indicator light, a color changing light or other feature, an audible alarm, a combination thereof, or the like. In one embodiment, indication feature 1006 is a color changing window.

The one or more sensors can be pressure sensors, airflow sensors, temperature sensors, $CO_2$ sensors, $O_2$ sensors, other gas sensors, aroma sensors, humidity sensors, combinations thereof, or the like. In one embodiment, at least one of the at least one sensors is a $CO_2$ sensor.

In some embodiments, sensor 1102 within device 1100 may not be electronic. The sensing system can be a chemical based system. In some embodiments, a chemical sensing system can provide a user with a visible chemical color change of an indicator. In one embodiment, a chemical $CO_2$ sensor can be used that changes a chemical compositions color if $CO_2$ is elevated beyond a particular level(s).

Devices such as device 106, device 202, or volume control mechanism 118 can be manufactured and/or sold as a standalone unit. Parts such as resuscitation interfaces and accompanying gas sources can be manufactured and/or sold separately. Devices can be packaged and appropriately sterilized per industry standard separately from resuscitation interfaces and accompanying gas sources.

In other embodiments, devices such as device 106, device 202, or volume control mechanism 118 can be manufactured and/or sold along with resuscitation interfaces and/or an accompanying gas source(s). In one embodiment, a device is manufactured and/or sold along with a resuscitation interface. In another embodiment, a device is manufactured and/or sold along with a gas source such as an ambu bag. In still other embodiments, a device is manufactured and/or sold along with a resuscitation interface and a gas source such as an ambu bag. In one embodiment, a device is manufactured and/or sold alone.

The devices described herein can be provided as kits. A kit can include a device as described herein and instructions for using the device.

In other embodiments, a kit can include a device as described herein, a resuscitation interface, and instructions for use.

In other embodiments, a kit can include a device as described herein, a resuscitation interface, a manual resuscitation gas source, and instructions for use.

In other embodiments, a kit can include a device as described herein, a resuscitation interface, a pressurized gas source connection fitting, and instructions for use.

In other embodiments, a kit can include a device as described herein, a manual resuscitation gas source, and instructions for use.

In other embodiments, a kit can include a device as described herein, a manual resuscitation gas source, an intubation tube, and instructions for use.

In other embodiments, a kit can include a device as described herein, an intubation tube, and instructions for use.

In other embodiments, a kit can include a device as described herein, a pressurized gas source connection fitting, an intubation tube, and instructions for use.

In some embodiments, the devices described herein are safe to at least one sterilization technique including, but not limited to gamma irradiation, pressure sterilization and/or steam sterilization.

The devices described herein can be configured as single use devices. In other words, the devices can be configured such that after a device is used on or for a patient, that device can be discarded. In other embodiments, the devices can be configured as reusable devices that can be appropriately cleaned and sterilized multiple times.

The following are non-limiting embodiments according to the present description.

Embodiment 1

An overinflation and/or overventilation device, the device comprising: a body configured to attach to a resuscitation interface and a gas source: a subject metric input component disposed at the body, the subject metric input component configured to receive input specifying a metric associated with a resuscitation subject; and a volume control mechanism disposed within the body, the volume control mechanism configured to control a volume of gas provided by the gas source during a manual resuscitation that is communicated to the resuscitation interface based on the metric provided by the subject metric input component.

Embodiment 2

The device of Embodiment 1, wherein the resuscitation interface includes a mask or an advanced airway.

Embodiment 3

The device of Embodiment 1, wherein the resuscitation gas source includes one or both of a resuscitation bag or an oxygen ($O_2$) source.

Embodiment 4

The device of Embodiment 1, wherein the body includes an inlet port and an outlet port, wherein one or both of the inlet port and the outlet port comply with a standard for manual resuscitator parts such that the device is insertable into existing standard resuscitation equipment.

Embodiment 5

The device of Embodiment 1, wherein the metric associated with the subject includes one or more of a weight, a range of weights, a height, a range of heights, a body habitus, a body mass index, an age, a range of ages, or a developmental stage.

Embodiment 6

The device of Embodiment 1, wherein the subject metric input component includes one or more of a dial, a keypad, a button, or a slider.

Embodiment 7

The device of Embodiment 1, wherein the volume control mechanism is configured to vent excess gas volume beyond the controlled volume.

Embodiment 8

The device of Embodiment 1, wherein the volume control mechanism includes two or more different diameter feed lines that correspond to a selection on the subject metric input component.

Embodiment 9

The device of Embodiment 1, further comprising a timing device configured to provide an indication to a healthcare provider performing manual resuscitation to convey a time period between rescue or assisted breaths.

Embodiment 10

The device of Embodiment 9, wherein the time period is determined based on the metric received by the subject metric input component.

Embodiment 11

The device of Embodiment 9, wherein the time period is determined such that a rate of rescue or assisted breaths at the controlled volume provided during manual resuscitation will result in a gas pressure threshold at the resuscitation interface remaining unbreached.

Embodiment 12

The device of Embodiment 9, wherein the indication includes feedback that is one or more of visual, audio, or haptic.

Embodiment 13

An overinflation and/or overventilation device, the device comprising: an inlet configured to receive a manual resuscitation gas source; an outlet configured to receive a resuscitation interface; and a body portion including a subject metric input component and a volume control mechanism, wherein the subject metric input component is configured to move the volume control mechanism based on a user input to achieve a portion of a gas volume received at the inlet that is delivered at the outlet.

Embodiment 14

The device of Embodiment 13, wherein the resuscitation interface includes a mask or an advanced airway, and wherein the manual resuscitation gas source includes one or both of a resuscitation bag or an oxygen ($O_2$) source.

Embodiment 15

The device of Embodiment 13, wherein the a subject metric input includes quadrants that indicate a metric associated with a subject, the metric includes one or more of a weight, a range of weights, a height, a range of heights, a body habitus, a body mass index, an age, a range of ages, or a developmental stage.

Embodiment 16

The device of Embodiment 13, wherein the subject metric input component is configured to spin the volume control mechanism.

Embodiment 17

The device of Embodiment 16, wherein the volume control mechanism is a disk that includes two or more different diameter feed lines.

Embodiment 18

The device of Embodiment 16, wherein the volume control mechanism is a conical stopper and that engages a lip.

Embodiment 19

The device of Embodiment 18, wherein the conical stopper includes one or more by-pass channels.

Embodiment 20

A method for manual resuscitator assembly operation involving adjustably controlling rescue or assisted breaths provided during manual resuscitation to prevent overinflation and/or overventilation, the method comprising: receiving input specifying a metric associated with a resuscitation subject via a subject metric input component disposed at a device, the device being disposed between a manual resuscitation gas source and a resuscitation interface by an inlet port of the device being attached to the manual resuscitation gas source and an outlet port of the device being attached to the resuscitation interface such that a portion of gas of a rescue or assisted breath provided during manual resuscitation is communicated from the manual resuscitation gas source via the inlet port to the resuscitation interface via the outlet port; controlling a volume of the portion of gas of the rescue or assisted breath provided during manual resuscitation that is communicated through the outlet port based on the metric received by the subject metric input component; and providing an indication to a healthcare provider performing manual resuscitation to convey a time period between rescue or assisted breaths.

Embodiment 21

A device configured to be disposed within a gas flow circuit of a manual resuscitator in order to adjustably control rescue or assisted breaths provided during manual resuscitation to prevent overinflation and/or overventilation, the device comprising: a body having an inlet port and an outlet port, the inlet port being configured to be attached to the gas flow circuit in fluid communication with a manual resuscitation gas source, the outlet port being configured to be attached to the gas flow circuit in fluid communication with a resuscitation interface such that a portion of gas of a rescue or assisted breath provided during manual resuscitation is communicated from the manual resuscitation gas source via the inlet port to the resuscitation interface via the outlet port; a subject metric input component disposed at the body, the subject metric input component being configured to receive input specifying a metric associated with a resuscitation subject; and a volume control mechanism disposed within the body, the volume control mechanism being configured to control a volume of the portion of gas of the rescue or assisted breath provided during manual resuscitation that is communicated through the outlet port based on the metric received by the subject metric input component.

Embodiment 22

A manual resuscitator assembly configured for adjustably controlling rescue or assisted breaths provided during manual resuscitation to prevent overinflation and/or overventilation, the assembly comprising: a manual resuscitation gas source; a resuscitation interface; and a device configured to adjustably control rescue or assisted breaths provided during manual resuscitation to prevent overinflation and/or overventilation, the device comprising: a body having an inlet port and an outlet port, the inlet port being attached in fluid communication with the manual resuscitation gas source, the outlet port being attached in fluid communication with the resuscitation interface such that a portion of gas of a rescue or assisted breath provided during manual resuscitation is communicated from the manual resuscitation gas source via the inlet port to the resuscitation interface via the outlet port; a subject metric input component disposed at the body, the subject metric input component being configured to receive input specifying a metric associated with a resuscitation subject; and a volume control mechanism disposed within the body, the volume control mechanism being configured to control a volume of the portion of gas of the rescue or assisted breath provided during manual resuscitation that is communicated through the outlet port based on the metric received by the subject metric input component.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific example embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Example embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. An overinflation and/or overventilation device, the device comprising:
    a body configured to attach to a resuscitation interface and a gas source;
    a subject metric input component disposed at the body, the subject metric input component configured to receive input specifying a metric associated with a resuscitation subject;
    a volume control mechanism disposed within the body, the volume control mechanism configured to control a volume of gas provided by the gas source, during a manual resuscitation, that is communicated to the resuscitation interface based on the metric provided by the subject metric input component;

a control unit for receiving data from a sensor associated with the subject metric input component, wherein the control unit and the sensor disposed within the body; and a timing device configured to provide an indication to a healthcare provider performing manual resuscitation to convey a time period between rescue or assisted breaths wherein the control unit is configured to determine the time period using the received data.

2. The device of claim 1, wherein the resuscitation interface includes a mask or an advanced airway.

3. The device of claim 1, wherein the resuscitation gas source includes one or both of a resuscitation bag or an oxygen ($O_2$) source.

4. The device of claim 1, wherein the body includes an inlet port and an outlet port, wherein one or both of the inlet port and the outlet port comply with a standard for manual resuscitator parts such that the device is insertable into existing standard resuscitation equipment.

5. The device of claim 1, wherein the metric associated with the subject includes one or more of a weight, a range of weights, a height, a range of heights, a body habitus, a body mass index, an age, a range of ages, or a developmental stage.

6. The device of claim 1, wherein the subject metric input component includes one or more of a dial, a keypad, a button, or a slider.

7. The device of claim 1, wherein the volume control mechanism is configured to vent excess gas volume beyond the controlled volume.

8. The device of claim 1, wherein the volume control mechanism includes two or more different diameter feed lines that correspond to a selection on the subject metric input component.

9. The device of claim 1, wherein the time period is determined such that a rate of rescue or assisted breaths at the controlled volume provided during manual resuscitation will result in a gas pressure threshold at the resuscitation interface remaining unbreached.

10. The device of claim 1, wherein the indication includes feedback that is one or more of visual, audio, or haptic.

11. An overinflation and/or overventilation device, the device comprising:

an inlet configured to receive a manual resuscitation gas source;

an outlet configured to receive a resuscitation interface;

a body portion including a subject metric input component and a volume control mechanism, wherein the subject metric input component is configured to move the volume control mechanism based on a user input to achieve a portion of a gas volume received at the inlet that is delivered at the outlet;

a control unit for receiving data from a sensor associated with the subject metric input component, wherein the control unit and the sensor disposed within the body portion; and a timing device, configured to provide an indication to a healthcare provider performing manual resuscitation to convey a time period between rescue or assisted breaths wherein the control unit is configured to determine the time period using the received data.

12. The device of claim 11, wherein the resuscitation interface includes a mask or an advanced airway, and wherein the manual resuscitation gas source includes one or both of a resuscitation bag or an oxygen ($O_2$) source.

13. The device of claim 11, wherein the subject metric input includes quadrants that indicate a metric associated with a subject, the metric including one or more of a weight, a range of weights, a height, a range of heights, a body habitus, a body mass index, an age, a range of ages, or a developmental stage.

14. The device of claim 11, wherein the subject metric input component is configured to spin the volume control mechanism.

15. The device of claim 14, wherein the volume control mechanism is a disk that includes two or more different diameter feed lines.

16. The device of claim 14, wherein the volume control mechanism is a conical stopper and that engages a lip.

17. The device of claim 16, wherein the conical stopper includes one or more by-pass channels.

18. A method for manual resuscitator assembly operation involving adjustably controlling rescue or assisted breaths provided during manual resuscitation to prevent overinflation and/or overventilation, the method comprising:

receiving input specifying a metric associated with a resuscitation subject via a subject metric input component disposed at a device, the device being disposed between a manual resuscitation gas source and a resuscitation interface, by an inlet port of the device being attached to the manual resuscitation gas source, and an outlet port of the device being attached to the resuscitation interface, such that a portion of gas of a rescue or assisted breath provided during manual resuscitation is communicated from the manual resuscitation gas source via the inlet port to the resuscitation interface via the outlet port;

providing a control unit for receiving data from a sensor associated with the subject metric input component, wherein the control unit and the sensor disposed within the device;

controlling a volume of the portion of gas of the rescue or assisted breath provided during manual resuscitation that is communicated through the outlet port based on the metric received by the subject metric input component; and providing an indication to a healthcare provider performing manual resuscitation via a timing device configured to convey a time period between rescue or assisted breaths wherein the control unit is configured to determine the time period using the received data.

* * * * *